(12) United States Patent  (10) Patent No.: US 8,537,020 B2
Thorson  (45) Date of Patent: Sep. 17, 2013

(54) VISUAL INDICATOR OF GAS SENSOR IMPAIRMENT

(75) Inventor: Walter R. Thorson, Calgary (CA)

(73) Assignee: Honeywell International Inc., Morristown, NJ (US)

( * ) Notice: Subject to any disclaimer, the term of this patent is extended or adjusted under 35 U.S.C. 154(b) by 648 days.

(21) Appl. No.: 12/342,894

(22) Filed: Dec. 23, 2008

(65) Prior Publication Data

US 2010/0156647 A1  Jun. 24, 2010

(51) Int. Cl.
*G08B 17/10* (2006.01)

(52) U.S. Cl.
USPC ......... 340/632; 340/521; 340/693.6; 73/1.06; 73/152.18; 73/23.2; 250/339.13; 250/341.2; 250/341.5

(58) Field of Classification Search
USPC .......... 340/632, 693.6, 521; 73/1.06, 152.18, 73/23.2, 1; 250/339.13, 341.2, 341.5
See application file for complete search history.

(56) References Cited

U.S. PATENT DOCUMENTS

| | | | | |
|---|---|---|---|---|
| 3,864,628 A * | 2/1975 | Klass et al. | ................... | 324/71.1 |
| 5,118,473 A * | 6/1992 | Coleman et al. | ............. | 422/68.1 |
| 5,538,620 A * | 7/1996 | Nikolskaja | ..................... | 205/782 |
| 6,244,093 B1 * | 6/2001 | Parekh | ........................... | 73/1.06 |
| 6,706,541 B1 * | 3/2004 | Toprac et al. | ..................... | 438/7 |
| 6,987,459 B2 * | 1/2006 | Tice | ............................... | 340/632 |
| 7,086,283 B2 * | 8/2006 | Koyano et al. | ................... | 73/431 |
| 7,089,779 B2 * | 8/2006 | Tajima et al. | ................... | 73/23.2 |
| 2001/0018844 A1 * | 9/2001 | Parekh | ........................... | 73/1.06 |
| 2004/0145485 A1 * | 7/2004 | Tice | ............................... | 340/632 |
| 2005/0016543 A1 * | 1/2005 | Geist | ........................ | 128/207.14 |
| 2005/0017206 A1 * | 1/2005 | Tice et al. | ....................... | 250/573 |
| 2006/0058697 A1 * | 3/2006 | Mochizuki et al. | ........... | 600/532 |
| 2006/0062688 A1 * | 3/2006 | Lawrence | ........................ | 422/56 |
| 2007/0042348 A1 * | 2/2007 | Amano et al. | ..................... | 435/5 |
| 2007/0102639 A1 * | 5/2007 | Cutler et al. | ............. | 250/339.13 |
| 2007/0241261 A1 * | 10/2007 | Wendt | ........................... | 250/221 |
| 2009/0164141 A1 * | 6/2009 | Lee | .................................... | 702/30 |
| 2010/0192683 A1 * | 8/2010 | Elkins | ......................... | 73/152.18 |

FOREIGN PATENT DOCUMENTS

| | | | | |
|---|---|---|---|---|
| CN | 101226166 A | * | 7/2008 | |
| JP | 10221301 A | * | 8/1998 | |
| JP | 2001041791 A | * | 2/2001 | |
| JP | 2001099799 A | * | 4/2001 | |
| JP | 2002257768 A | * | 9/2002 | |
| JP | 2002312870 A | * | 10/2002 | |
| JP | 2007249501 A | * | 9/2007 | |
| WO | WO 0079305 A1 | * | 12/2000 | |
| WO | WO 0186260 A1 | * | 11/2001 | |
| WO | WO 2010070360 A1 | * | 6/2010 | |

* cited by examiner

*Primary Examiner* — George Bugg
*Assistant Examiner* — Paul Obiniyi
(74) *Attorney, Agent, or Firm* — Husch Blackwell LLP

(57) ABSTRACT

A gas detector includes at least one gas sensing element and a calorimetric sensing material for detection of a different, potentially contaminating gas which can impair the function of the gas sensing element disposed within the detector. The sensing material provides a visual indication of the presence of the potentially contaminating gas.

10 Claims, 7 Drawing Sheets

VISUAL INDICATOR OF GAS SENSOR IMPAIRMENT

FIELD

The present invention relates generally to gas detectors, and especially to devices, systems and methods for sensing and indicating the presence of chemicals or compounds that impair the performance or function of the gas sensor(s) disposed within a gas detector.

BACKGROUND

Portable electronic gas detectors are well known means of monitoring for hazardous gases in various environments. Such detectors typically include one or more gas sensors, and electronics to convert the output signal from each sensor into one or more signals representative of the concentration of the gas being monitored. Many types of gas sensors are well known in the art, including for example, electrochemical gas sensors for toxic or asphyxiate gases, catalytic bead (pellistor) gas sensors for combustible gases, and galvanic gas sensors for Oxygen.

FIGS. 1, 1A illustrate a known multi-gas detector 10. Detector 10 includes a housing 12 which carries a plurality 14 of electro-chemical gas sensors 14$a$, $b$, $c$, $d$. Each of the sensors includes a gas inflow port such as 14$a$-1. Each of the sensors is covered with a gas permeable membrane such as 14$a$-2 as would be understood by those of skill in the art to protect the respective sensor from inflowing particulate matter.

Housing 12 can also carry a visual display 16, with perhaps an output port 16-1 for an audio and/or visual alarm. Control circuitry, illustrated in phantom at 18, can be coupled to the sensors 14, display 16 and associated audio/visual output device to provide visual and audio indicators as to a concentration of one of more sensed gases. Control element 20 can be used to select a gas, or gasses to detect and evaluate.

FIG. 2 illustrates a known gas sensor 14$i$. Sensor 14$i$ can be any one of known electrochemical gas sensors as would be understood by those of skill in the art. Sensor 14$i$ includes an input port 14$i$-1 formed in a housing 14$i$-3. The inflow port 14$i$-1 is covered by a gas permeable membrane 14$i$-2. Multiple electrodes, for example, three electrodes, are electrically connected to signal pins 14$i$-4 extending from housing 14$i$-3 and can be coupled to control circuits such as 18.

Although much progress has been made in improving the performance and robustness of gas sensors, such as the sensors of the plurality 14, a number of problems persist. Gas detectors, such as detector 10 are often used in harsh environments where the gas sensors may be exposed to chemicals in the atmosphere that damage, interfere with, or alter the response of a gas sensor to the gas it is intended to sense.

By way of example, typical chemistries for electrochemical gas sensors for detection of hydrogen sulfide gas often exhibit cross-sensitivity to ethanol or methanol vapors, and typical electrochemical carbon monoxide sensors exhibit cross-sensitivity to hydrogen. It is also known that high concentrations of certain solvent vapors can impair the function of an electrochemical gas sensor by promoting electrolyte flooding within the porous electrode structure or by promoting wetting of the supporting diffusion membrane materials of the electrochemical cell.

In general these types of interactions are problematic. They can lead to a number of undesirable outcomes including inaccurate measurements of gas concentration, increased probability of false alarms, reduced sensitivity, delayed sensor responsiveness to a target gas, or even to permanent impairment or failure of the gas sensor.

In practice, manufacturers recommend regular verification of sensor operation by performing a functional test (commonly referred to as a bump test) in which the gas sensors are exposed to a gas mixture of known, fixed composition of one or more analyte gases that the detector is designed to detect. Typically, the concentration of analyte in the test gas is sufficient to trigger an alarm response in a properly functioning gas detector, thereby providing verification of a sensor's response to gas as well as functional verification of the alarm indicating means disposed within the gas detector.

Additionally, a number of electrical sensor interrogation techniques have been developed to provide a means of evaluating the condition of electrochemical gas sensors. These methods are able to identify a number of common failure modes inside the sensor, including for example, loss of electrical continuity within the sensor, or changes in the internal resistance of the sensor.

While these advances offer some improvements in the ability to verify some aspects of sensor functionality, they do not provide a means to alert the user to the presence of gases in the atmosphere that could be causing inaccurate readings or damage to the gas sensors while the detector is operating.

It is thus desirable to develop improved means for detecting and indicating the presence of chemicals or compounds that can impair the performance or function of a gas detector while it is operational and monitoring the atmosphere.

Colorimetric means of gas detection and indication are also known in the art. Examples of available calorimetric gas detection products include Draeger Tubes, available from Draeger Safety of Germany, and Chemcassette Tapes, available from Honeywell Analytics (formerly MDA Scientific) of the United States. Colorimetric techniques and chemistries have been developed over the years to detect several hundred different chemicals and compounds.

Typically the chemical formulation of a colorimetric sensing material is developed to produce a material that will undergo a lasting color change upon exposure to and chemical reaction with the analyte of interest. The persistence of the change in color of the sensing material is desirable in these applications since it can be used to provide a physical record of the chemical measurement being taken.

DETAILED DESCRIPTION

Figure 1:
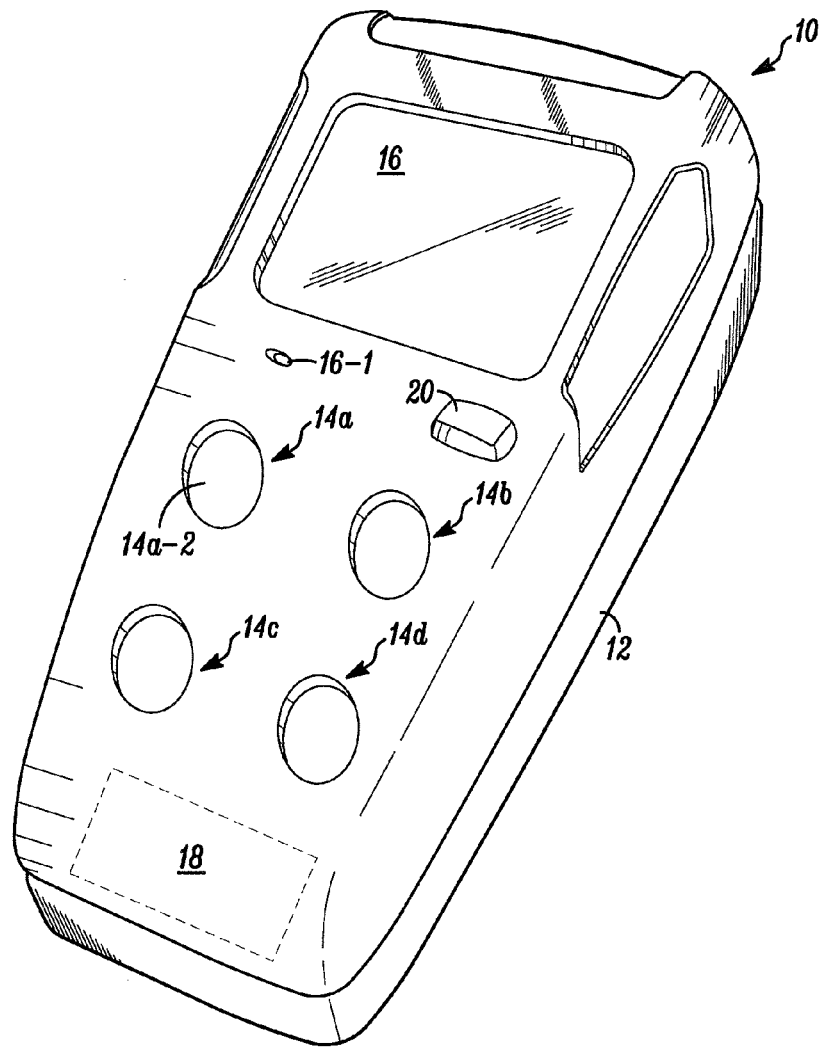
FIG. 1 illustrates a prior art portable gas detector.
Figure 1A:
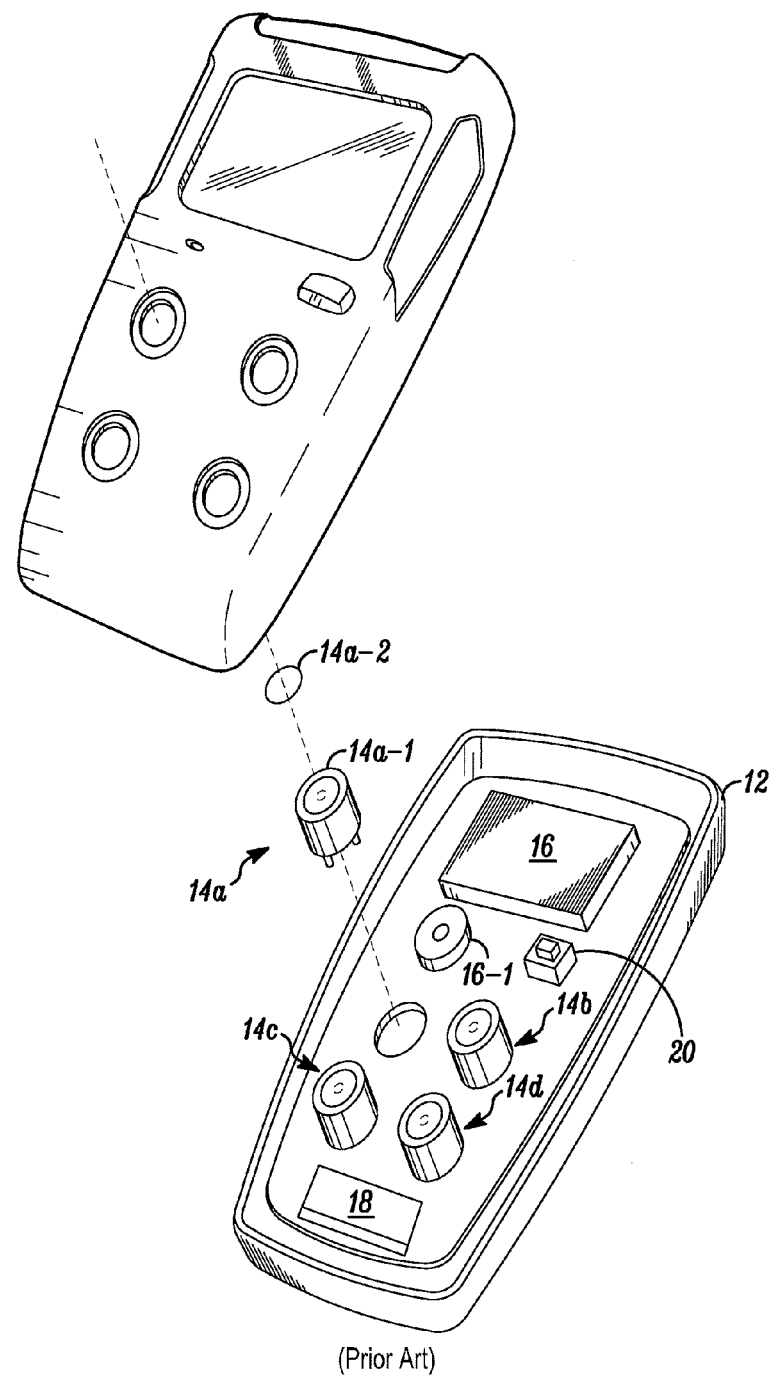
FIG. 1A is an exploded view of the detector of FIG. 1.
Figure 2:
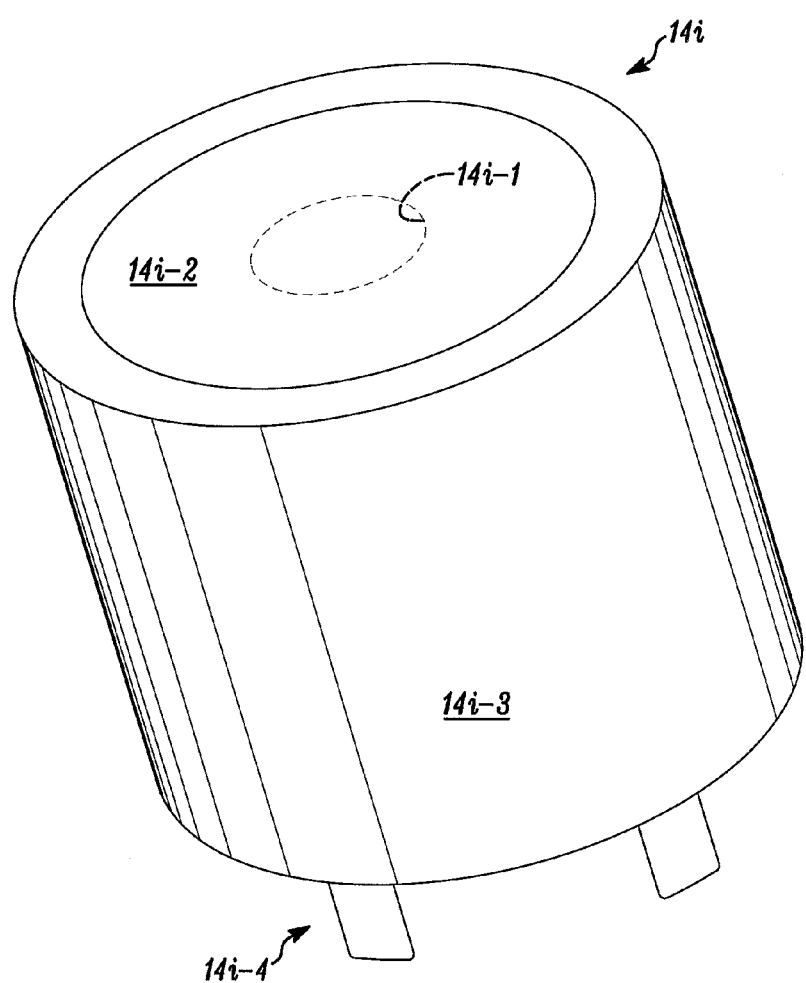
FIG. 2 illustrates a prior art three electrode electrochemical gas sensor.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In a first embodiment of the invention, a suitable calorimetric material or a plurality of such materials can be disposed within a portable gas detector in such a way that those materials can interact with the ambient atmosphere by way of ordinary gas diffusion. For example, but not by way of limitation, the calorimetric materials can be deposited by any suitable process onto any suitable exterior surface of the gas detector, for example by means of screen printing. Many other suitable methods of fabricating and disposing the calorimetric sensing material within the gas detector will be evident to those skilled in the art, including, but not limited to various methods of printing, dispensing, molding, impregnating, bonding etc.

In yet another embodiment of the invention, a gas detector carries calorimetric material, which can be printed or otherwise disposed upon a gas permeable membrane as is typically used to protect the gas detector's sensors from liquid ingress or other types of liquid or particulate contamination. In this embodiment, a plurality of like or different colorimetric formulations corresponding to specific chemicals that are harmful to the different types of gas sensors can be disposed on, or adjacent to the location or inlet corresponding to each of the gas sensors within the instrument. The user of the instrument is thus provided a useful visual indicator of the presence of a potentially harmful or interfering chemical and this indication easily visually associated with the affected gas sensor or sensors.

In another embodiment of the invention, one or more colorimetric indicator materials are disposed in a suitable arrangement upon a diagnostic card, each of the individual colorimetric indicators corresponding to a specific chemical known to interfere with the desired operation of a gas detector. The purpose of such a card is to provide a troubleshooting or training aid for use by industrial hygienists or other field personnel in the event or repeated or suspected problems affecting gas detection equipment in a locale.

In the above described embodiment, the diagnostic card can be packaged in such manner that said calorimetric indicators are suitably protected against exposure to the atmosphere until the time of use, and the calorimetric indicator materials used can be single use materials that undergo a lasting color change upon exposure to the analyte that each indicator is designed to detect. For example, a diagnostic card employing a plurality of calorimetric indicators sensitive to various organo-silicones, hydrides, organo-metallic compounds, phosphates and other chemicals known to poison catalytic bead pellistor gas sensors could be used to troubleshoot problems at a site experiencing a higher than expected rate of pellistor sensor problems or sensor failures.

In another embodiment of the invention, one or more calorimetric indicating materials can be disposed within or adjacent to the inlet aperture of an individual gas sensor. The deposited material(s) could be used to visually indicate whether the gas sensor has been exposed to a particular harmful chemical or class of chemicals.

It will be understood that in embodiments of the present invention, a permanent color change of the indicating material is not always necessary and may be undesirable for the realization of certain practical embodiments of the invention. A colorimetric chemistry which provides a temporary color change only while the indicating material is exposed to a suitable concentration of the analyte of interest, and which subsequently returns to its original color when the analyte is not longer present in detectable quantities, is useful in implementing embodiments of the invention described herein. The chemical formulations and underlying principles of such temporary or reversible indicators, as would be understood by those of skill in the art, are a function of adsorption and desorption of the detected analyte in the matrix of the colorimetric material, and its chemical interaction with the colorimetric material while it is adsorbed therein.

Figure 3:
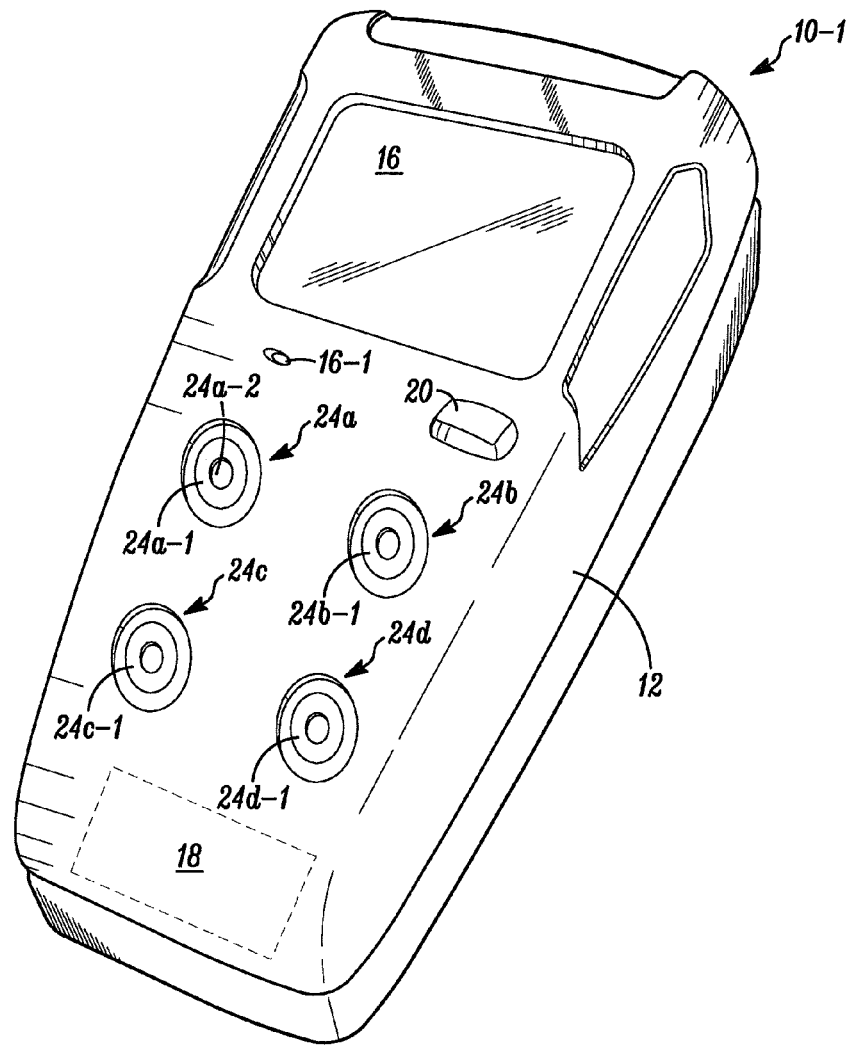
FIG. 3 illustrates a first embodiment of a gas detector in accordance with the invention.
Figure 3A:
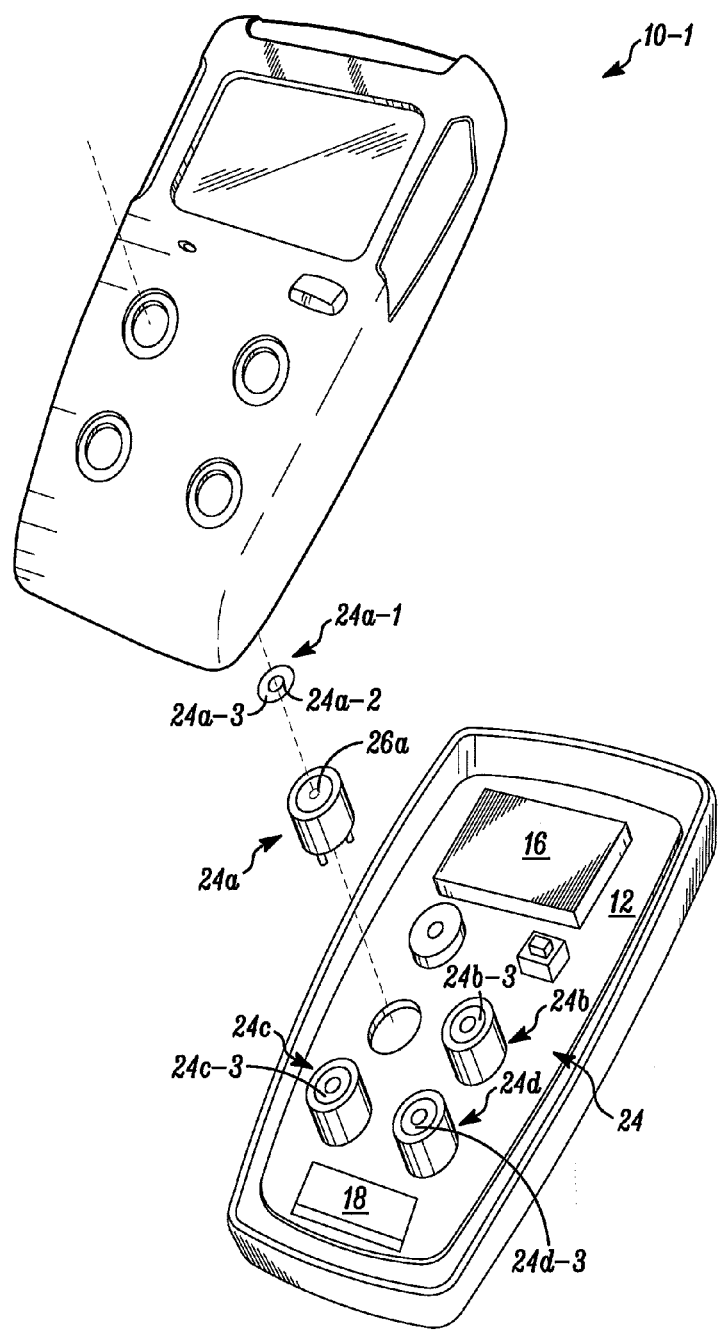
FIG. 3A is an exploded view of the detector of FIG. 3.

FIGS. 3, 3A illustrate a multi-gas detector 10-1 which embodies the invention. Structures of the detector 10-1 which are the same as corresponding structures of the detector 10 of FIG. 1 have the same identification numerals and were discussed previously.

Detector 10-1 carries a plurality of gas sensors 24. The members of the plurality 24, such as 24$i$, respond to different selected gases. Each of the sensors, such as 24$a$, carries a gas permeable membrane such as 24$a$-1. In the detector 10-1 each membrane such as 24$a$-1 has a central region 24$a$-2 through which gas can pass to enter the sensor, via inflow port 26$a$. The region 24$a$-2 is preferably surrounded by an annular region, such as region 24$a$-3 which carries one or more calorimetric materials. The calorimetric materials are selected, based on the characteristics of the respective sensor, such as sensor 24$a$, and interact with contaminants in the ambient atmosphere.

The calorimetric materials in the regions such as 24$a$-3, $b$-3, $c$-3, $d$-3 can be deposited by any suitable process onto any suitable exterior surface of the gas sensors of the plurality 24, for example by means of screen printing, dispensing, molding, impregnating, bonding all without limitation. The regions such as 24$a$-3, $b$-3, $c$-3 and $d$- can carry one or more calorimetric materials which can visually indicate the presence of a variety of different gasses which are adverse to the operation of the respective sensor, such as 24$a$. Alternately, the colorimetric material(s) carrying regions can be carried by the housing 12.

Figure 4:
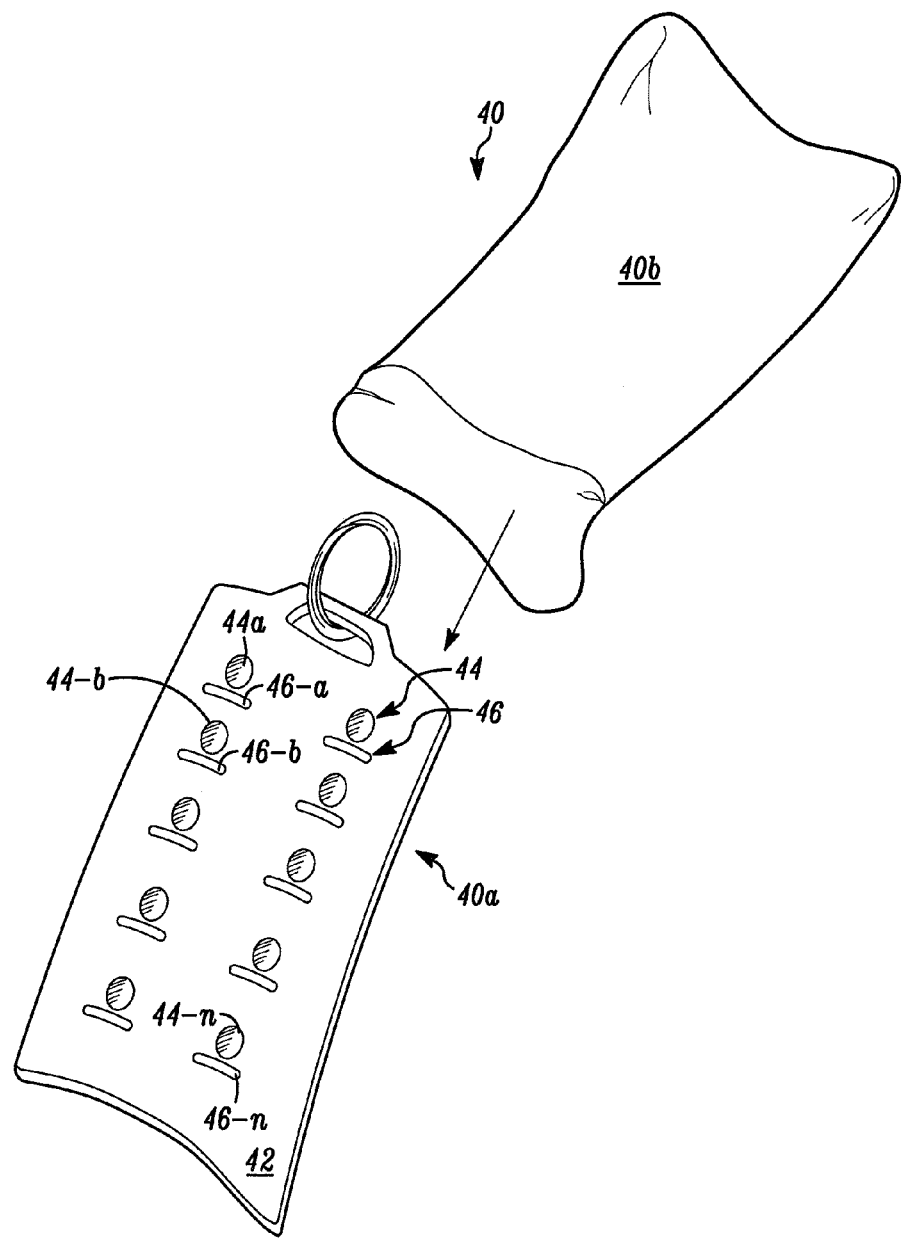
FIG. 4 illustrates another embodiment of the invention.

FIG. 4 illustrates an indicator assembly which includes a planar gas identifier element 40$a$ and an associated heat sealable delivery/storage pouch 40$b$. The element 40$a$ can be provided to a user in the sealed pouch 40$b$ and only removed therefrom when the user wants to obtain an indication of the presence of various gases that might have a deleterious effect on one or more individuals, or, gas detectors in the region.

The element 40$a$ can carry a plurality 44 of colorimetric sensing materials such as 44-$a$, -$b$, -$c$ . . . -$n$. These materials can exhibit either a one-time non-reversible color change in the presence of a selected gas. Alternately, some or all of them can be reversible. A textual identifier such as members 46-$a$, -$b$, -$c$ -$n$ of a plurality 46 of such identifiers can be associated with each of the colorimetric sensing regions 44-$i$. The card, or element 40$a$ can provide a troubleshooting or training aid for use by industrial hygienists or other field personnel in the event or repeated or suspected problems with undesirable gases in a region. Where non-reversible color change calorimetric sensing materials are used, the card 40$a$ provides permanent evidence of the presence of selected, undesirable gases.

Figure 5:
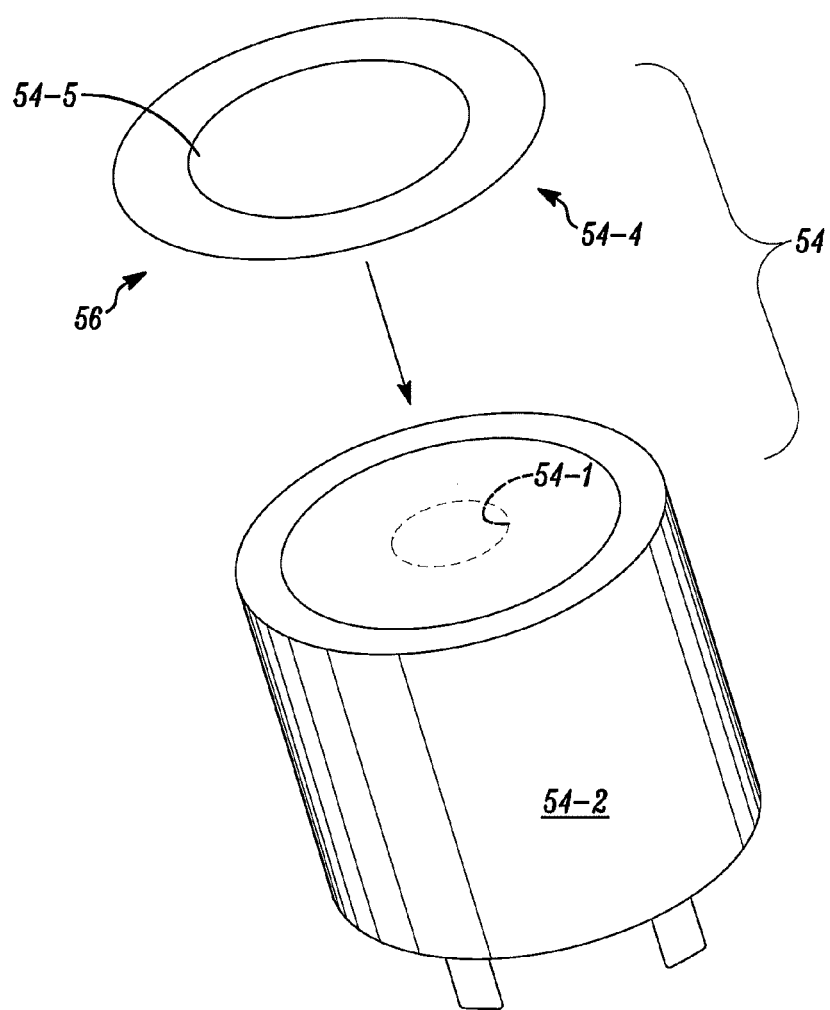
FIG. 5 illustrates a third embodiment of the invention.

FIG. 5 illustrates an electro-chemical gas sensor 54. Sensor 54 has a housing 54-2 which carries a gas inflow port 54-1, and a plurality of electrical connectors 54-3. A membrane 56 covers the inflow port 54-1.

A region 54-4 carrying one or more calorimetric indicating materials surrounds a central region 54-5 of the gas permeable membrane 56. The colorimetric indicating materials can be carried within or on the membrane 56 as discussed above. Also, as discussed above, the purpose of the membrane 56 is to protect the sensor 54 from various types of contamination. The region 54-4 is intended to provide a visual indicator of the presence of contaminating gases in the vicinity of the sensor 54.

The process by which the colorimetric indicating material, or materials are deposited on or placed on or in the region 54-4 is not a limitation of the invention. It will also be understood that the details of the respective gas sensors are not limitations of the invention. Further, other types of sensors can be incorporated without departing from the spirit and scope of the invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas detector comprising:
    a housing with at least one gas inflow port;
    an electro-chemical gas sensor carried in the housing, adjacent to the gas inflow port, the gas sensor responding to a first gas; and
    a plurality of colorimetric materials visible, at least in part, from outside of the housing, the colorimetric materials responding to at least a second, different gas, where the colorimetric materials detect and indicate the presence of chemicals or compounds that impair the performance or function of the electro-chemical gas sensor in a region monitored by the electro-chemical gas sensor, the colorimetric materials are printed on the housing or on a member carried by the housing; and
    a gas permeable member carried by the housing in a vicinity of the at least one gas inflow port, wherein a central region of the gas permeable membrane passes the first gas to the electro-chemical gas sensor, and wherein an outer annular region of the gas permeable membrane carries at least one of the plurality of colorimetric materials.

2. A detector as in claim 1 where the colorimetric material is one of printed on, molded into, imprinted into or bonded to the gas permeable membrane.

3. A detector as in claim 1 where the gas permeable member covers at least a portion of the at least one gas inflow port.

4. A detector as in claim 1 where the gas permeable member carries a plurality of different calorimetric materials where each of the plurality of different calorimetric materials responds to at least one gas different from the first gas.

5. A detector as in claim 1 where the housing defines a first surface which defines a plurality of spaced apart gas inflow ports.

6. A detector as in claim 5 where the housing carries a plurality of gas sensors, with each such sensor positioned adjacent to one of the Inflow ports with members of a plurality of calorimetric materials associated with each member of the plurality of gas sensors in the vicinity of a respective inflow port.

7. A detector as in claim 6 where members of the plurality of gas sensors comprise electro-chemical gas sensors.

8. A gas sensor comprising:
    a housing;
    an electro-chemical gas responsive structure responsive to a first gas carried in the housing;
    a gas inflow port defined by the housing;
    a plurality of gas responsive colorimetric materials printed on or carried by the housing, the plurality of gas responsive colorimetric materials are responsive at least to a second, different gas, the plurality of colorimetric materials detect and indicate the presence of chemicals or compounds that impair the performance or function of the electro-chemical gas responsive structure in a region monitored by the electro-chemical gas responsive structure; and
    a membrane carried by the housing or the gas responsive structure, wherein a central region of the membrane passes gas to the gas responsive structure, and wherein an outer annular region of the membrane carries at least one of the plurality of gas responsive colorimetric materials.

9. A sensor as in claim 8 where the annular region of the membrane surrounds the gas inflow port, at least in part.

10. A sensor as in claim 9 which carries a plurality of colorimetric materials, each of which is substantially responsive to a different gas where members of the plurality are at least in part positioned adjacent to the gas inflow port, and where each of the members of the plurality of colorimetric materials responds to at least one gas different from the first gas.

* * * * *